United States Patent
Mikuszeit et al.

(10) Patent No.: US 10,779,892 B2
(45) Date of Patent: Sep. 22, 2020

(54) TRACKING A CYLINDRICAL OPENING

(71) Applicant: Northern Digital Inc., Waterloo (CA)

(72) Inventors: Nikolai Mikuszeit, Radolfzell (DE); Christian Schilling, Thayngen (CH); Olaf Zerres, Radolfzell (DE); Georg Brunner, Constance (DE); Stefan R. Kirsch, Radolfzell (DE); Westley D. Ashe, Hinesburg, VT (US); Mark Robert Schneider, Williston, VT (US); Vladimir F. Kogan, Shelburne, VT (US)

(73) Assignee: Northern Digital Inc., Waterloo (CA)

( * ) Notice: Subject to any disclaimer, the term of this patent is extended or adjusted under 35 U.S.C. 154(b) by 0 days.

(21) Appl. No.: 16/047,112

(22) Filed: Jul. 27, 2018

(65) Prior Publication Data

US 2019/0046273 A1 Feb. 14, 2019

Related U.S. Application Data

(60) Provisional application No. 62/543,713, filed on Aug. 10, 2017.

(51) Int. Cl.
| | |
|---|---|
| *A61B 17/17* | (2006.01) |
| *A61B 17/72* | (2006.01) |
| *A61B 34/20* | (2016.01) |
| *G01D 5/20* | (2006.01) |
| *A61L 31/02* | (2006.01) |
| *A61B 90/00* | (2016.01) |
| *A61B 17/00* | (2006.01) |

(52) U.S. Cl.
CPC .......... *A61B 34/20* (2016.02); *A61B 17/1707* (2013.01); *A61B 17/1725* (2013.01); *A61B 17/72* (2013.01); *A61L 31/028* (2013.01); *G01D 5/202* (2013.01); *G01D 5/2046* (2013.01); *A61B 2017/00004* (2013.01); *A61B 2017/00876* (2013.01); *A61B 2034/2051* (2016.02); *A61B 2090/3954* (2016.02); *A61B 2090/3958* (2016.02)

(58) Field of Classification Search
CPC .............. A61B 17/72–7291; A61B 17/74–748
USPC .................................................... 606/62–68
See application file for complete search history.

(56) References Cited

U.S. PATENT DOCUMENTS

| | | | |
|---|---|---|---|
| 2,753,469 | A | 7/1956 | Statham et al. |
| 3,306,113 | A | 2/1967 | Tuccinardi |
| 3,516,294 | A | 6/1970 | Schmieder |
| 4,023,278 | A | 5/1977 | Hoyt |
| 4,047,439 | A | 9/1977 | Russell et al. |
| 4,557,667 | A | 12/1985 | Delassus et al. |

(Continued)

*Primary Examiner* — Nicholas J Plionis
(74) *Attorney, Agent, or Firm* — Fish & Richardson P.C.

(57) ABSTRACT

A system comprising: a sensor configured to be introduced into a clearance hole of a surgical implant, wherein the sensor is configured to be introduced in proximity to a generated magnetic field and cause distortion of the magnetic field; and one or more field measuring coils configured to: measure a characteristic of the magnetic field when the sensor is in proximity to the magnetic field; and provide, to a computing device, a signal representative of the measured characteristic of the magnetic field, wherein the computing device is configured to determine one or both of a position and an orientation of the sensor and the clearance hole based on the measured characteristic of the magnetic field.

21 Claims, 7 Drawing Sheets

(56) References Cited

U.S. PATENT DOCUMENTS

| | | |
|---|---|---|
| 4,718,276 A | 1/1988 | Laughlin |
| 4,808,079 A | 2/1989 | Crowley et al. |
| 4,818,185 A | 4/1989 | Alexeff |
| 4,905,517 A | 3/1990 | Crowe et al. |
| 4,922,753 A | 5/1990 | Idogaki et al. |
| 4,984,463 A | 1/1991 | Idogaki et al. |
| 4,991,438 A | 2/1991 | Evans |
| 5,007,292 A | 4/1991 | Crowe et al. |
| 5,461,919 A | 10/1995 | Laughlin |
| 5,665,912 A | 9/1997 | Laughlin |
| 5,780,741 A | 7/1998 | Raj |
| 5,908,987 A | 6/1999 | Raj |
| 6,173,611 B1 | 1/2001 | Laughlin |
| 6,374,673 B1 | 4/2002 | Schendel |
| 7,074,175 B2 | 7/2006 | Handy et al. |
| 7,175,912 B2 | 2/2007 | Cui et al. |
| 7,178,399 B2 | 2/2007 | Simonenko et al. |
| 7,204,581 B2 | 4/2007 | Peeters |
| 7,296,469 B2 | 11/2007 | Simonenko et al. |
| 7,700,193 B2 | 4/2010 | Chen et al. |
| 7,819,795 B1 | 10/2010 | Seeney et al. |
| 8,906,019 B2 | 12/2014 | Mueller |
| 8,944,067 B2 | 2/2015 | Robinson et al. |
| 9,017,713 B2 | 4/2015 | Tishin et al. |
| 9,186,317 B2 | 11/2015 | Smyth et al. |
| 9,196,405 B2 | 11/2015 | Schlenoff et al. |
| 2005/0119725 A1 | 6/2005 | Wang et al. |
| 2006/0282168 A1* | 12/2006 | Sherman ............ A61B 17/1707 623/18.12 |
| 2007/0264199 A1 | 11/2007 | Labhasetwar et al. |
| 2010/0145337 A1* | 6/2010 | Janna ................. A61B 17/1707 606/67 |
| 2010/0274256 A1* | 10/2010 | Ritchey .................... A61B 5/05 606/96 |
| 2012/0226094 A1* | 9/2012 | Ritchey .............. A61B 17/1707 600/12 |
| 2014/0052020 A1* | 2/2014 | Allen ................. A61B 10/0045 600/562 |
| 2014/0081121 A1* | 3/2014 | Wilhelm ................ A61B 17/80 600/409 |
| 2016/0113683 A1* | 4/2016 | Cheng .................... A61F 5/028 606/258 |
| 2018/0353304 A1* | 12/2018 | Govari ............... A61B 17/1707 |

\* cited by examiner

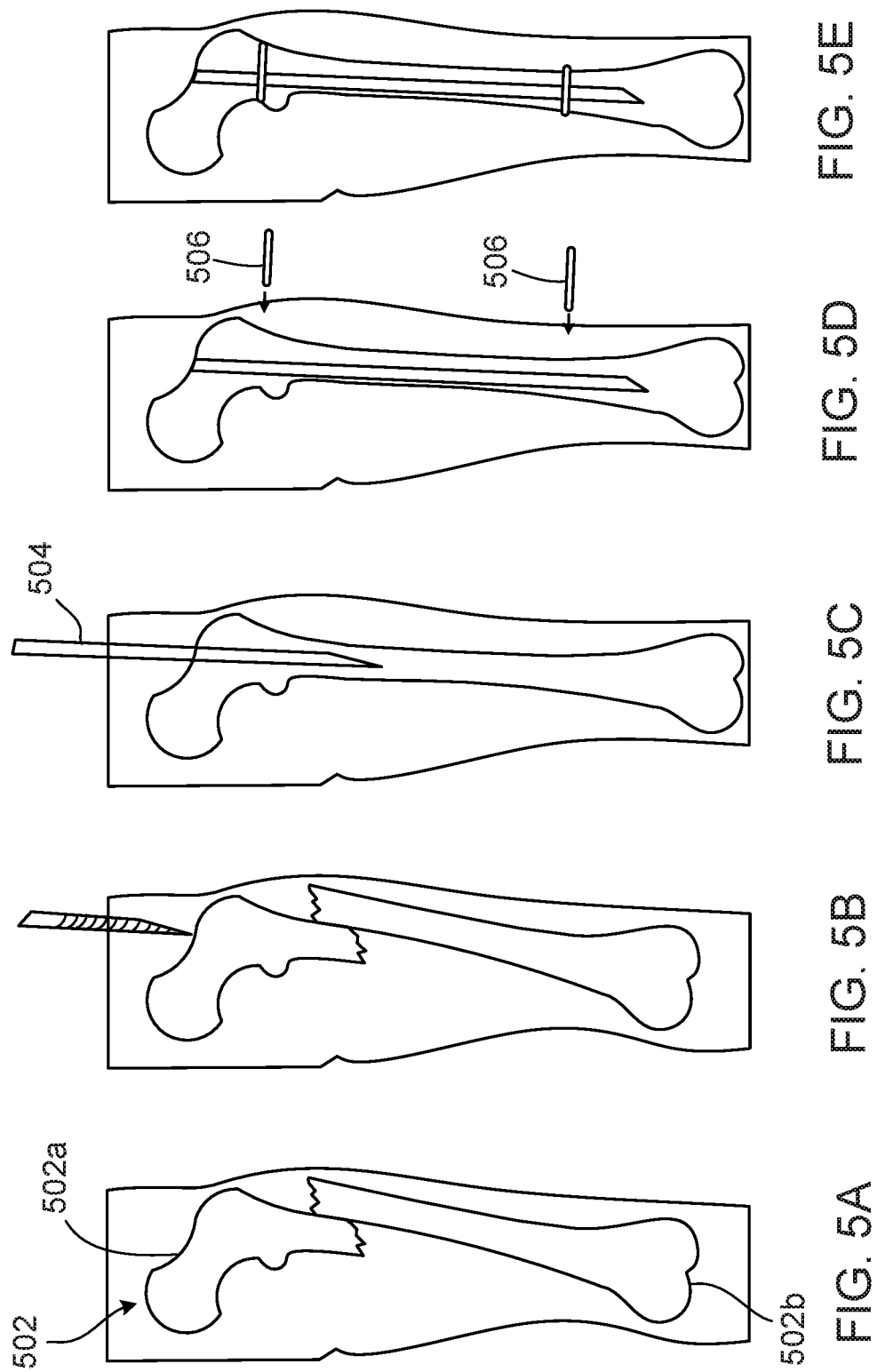

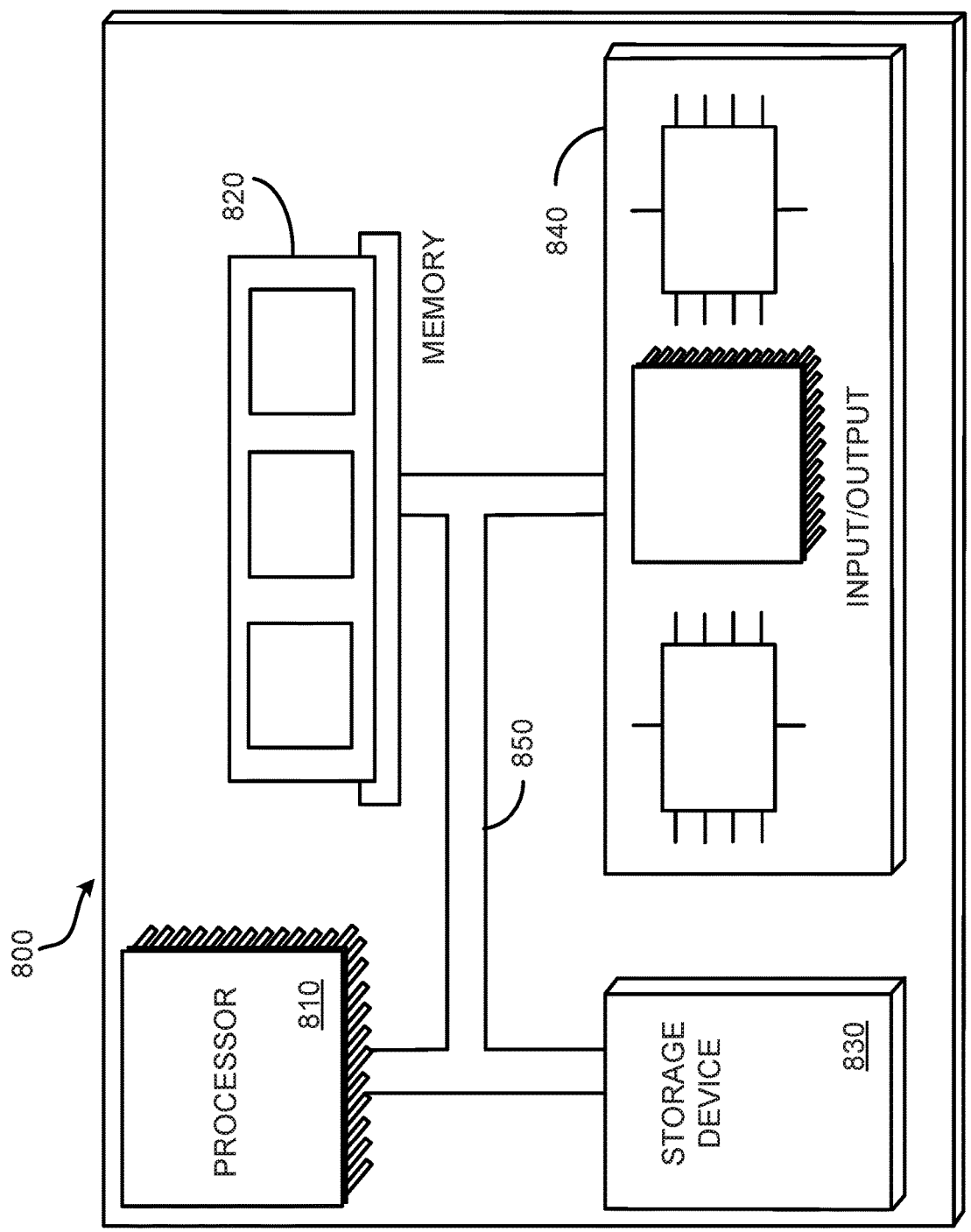

TRACKING A CYLINDRICAL OPENING

CLAIM OF PRIORITY

This application claims priority under 35 USC § 119(e) to U.S. Patent Application Ser. No. 62/543,713, filed on Aug. 10, 2017, the entire contents of which are hereby incorporated by reference.

TECHNICAL FIELD

This disclosure relates to tracking a cylindrical opening.

BACKGROUND

Electromagnetic Tracking (EMT) systems are used to aid location of instruments and anatomy in medical procedures, virtual reality (VR) settings, and augmented reality (AR) settings, among others. Such systems can determine a position of a sensor based on measured distortion of a transmitted magnetic field.

SUMMARY

An Electromagnetic Tracking (EMT) system can be used to track a medical device during a medical procedure. For example, in a surgical setting, the EMT system can be used to track the position and/or orientation of a surgical implant, such as an intramedullary (IM) nail during a surgical procedure. In particular, the position and/or orientation of one or more clearance holes of the IM nail can be tracked by tracking the position and/or orientation of a wireless sensor positioned within each clearance hole. In some implementations, the sensor may include a shell filled with a ferrofluid core. Magnetic properties of the sensor are configured to cause distortion in a generated magnetic field, and a field measuring coil is configured to measure characteristics of the distortion and provide such measurements to a computing device. The computing device can then determine the position and/or orientation of the sensor (and, e.g., the position and/or orientation of the clearance hole of the IM nail) based on the received measurements.

In some implementations, both the clearance hole and the sensor have a cylindrical shape and are cylindrically symmetrical. Thus, the roll component of the orientation of the sensor need not be tracked. Therefore, the sensor may be a five degree of freedom (5DoF) sensor while still determining the precise position and orientation of the clearance hole, thereby simplifying the tracking, allowing lower-cost hardware to be used, and minimizing the amount of computational power required for the computing device to determine the position and orientation of the clearance hole.

In some implementations, positioning the sensor within a clearance hole can provide a number of advantages. During implanting, the IM nail may experience external forces. Such external forces may naturally occur due to stress applied to the nail (e.g., when the IM nail is hammered into a bone). Such external forces may cause the IM nail to bend. The bend may cause the position and orientation of the clearance hole relative to a sensor that is not positioned within the clearance hole to change, thereby resulting in positioning errors. On the other hand, if the sensor is positioned within the clearance hole, changes to the position and orientation of the clearance hole due to deformation of the IM nail are correspondingly experienced by the sensor.

In some implementations, once the surgical procedure has concluded, some or all of the sensor may be removed from the IM nail and the patient's body. For example, the ferrofluid may be removed by piercing the shell and magnetically pulling the ferrofluid out of the body using a permanent magnet. The shell may then be removed. Alternatively, the shell may be made of a biocompatible and/or biodegradable material, and as such, may be left in the patient's body.

In one aspect, a system includes a sensor configured to be introduced into a clearance hole of a surgical implant. The sensor is configured to be introduced in proximity to a generated magnetic field and cause distortion of the magnetic field. The system also includes one or more field measuring coils configured to measure a characteristic of the magnetic field when the sensor is in proximity to the magnetic field. The one or more field measuring coils are also configured to provide, to a computing device, a signal representative of the measured characteristic of the magnetic field. The computing device is configured to determine one or both of a position and an orientation of the sensor and the clearance hole based on the measured characteristic of the magnetic field.

Implementations can include one or more of the following features.

In some implementations, the surgical implant is an intramedullary (IM) nail.

In some implementations, the IM nail is inserted into a femur of a patient.

In some implementations, a fastener is inserted into the clearance hole from a location at the exterior of a leg of the patient. The location at the exterior of the leg of the patient is identified based on the determined one or both of the position and an orientation of the sensor and the clearance hole.

In some implementations, the sensor has a cylindrical shape.

In some implementations, the sensor and the clearance hole are cylindrically symmetrical.

In some implementations, a diameter of the sensor is substantially equal to a diameter of the clearance hole.

In some implementations, the sensor is a five degree of freedom (5DoF) sensor.

In some implementations, the sensor includes a shell that contains a ferrofluid.

In some implementations, one or both of the shell and the ferrofluid are one or both of biocompatible and biodegradable.

In some implementations, the ferrofluid includes one or both of a liquid and a powder.

In some implementations, the ferrofluid includes superparamagnetic iron oxide nanoparticles (SPIONs).

In some implementations, the SPIONs include one or both of magnetite ($Fe_3O_4$) and maghemite ($\gamma\text{-}Fe_2O_3$).

In some implementations, the shell includes a polymer.

In some implementations, the ferrofluid is configured to be removed from the shell by piercing the shell and introducing a magnetic force in proximity to the shell.

In some implementations, the shell is pierced by a fastener that is inserted into the clearance hole.

In some implementations, the sensor is wireless.

In another aspect, a method includes introducing a sensor into a clearance hole of a surgical implant. The sensor is configured to be introduced in proximity to a generated magnetic field and cause distortion of the magnetic field. The method also includes receiving, from one or more field measuring coils, a signal representative of a characteristic of the magnetic field measured when the sensor is in proximity to the magnetic field. The method also includes determining one or both of a position and an orientation of the sensor and the clearance hole based on the measured characteristic of the magnetic field.

Implementations can include one or more of the following features.

In some implementations, the method also includes receiving, from the one or more field measuring coils, a signal representative of a characteristic of the magnetic field measured when the sensor is not in proximity to the magnetic field.

In some implementations, determining one or both of the position and the orientation of the sensor and the clearance hole includes comparing the characteristic of the magnetic field measured when the sensor is not in proximity to the magnetic field and the characteristic of the magnetic field measured when the sensor is in proximity to the magnetic field.

The details of one or more embodiments of the subject matter described herein are set forth in the accompanying drawings and the description below. Other features, objects, and advantages of the subject matter will be apparent from the description and drawings, and from the claims.

DESCRIPTION OF DRAWINGS

FIGS. 5A-E show a series of diagrams illustrating an intramedullary (IM) nail being inserted into a fractured femur.

FIG. 8 is a block diagram of an example computer system.

Like reference symbols in the various drawings indicate like elements.

DETAILED DESCRIPTION

An Electromagnetic Tracking (EMT) system can be used in medical settings, virtual reality (VR) settings, augmented reality (AR) settings, etc., to track a device. For example, in a surgical setting, the EMT system can be used to track medical equipment, robotic arms, etc., thereby allowing the three-dimensional location and the orientation of the device to be known to a medical professional (e.g., a surgeon) during a medical procedure. Such electromagnetic tracking within the body of a patient can be used for guidance purposes in image-guided procedures, and in some cases may allow for reduced reliance on other imaging modalities, such as fluoroscopy, which can expose the patient to health risk of ionizing radiation.

Figure 1:
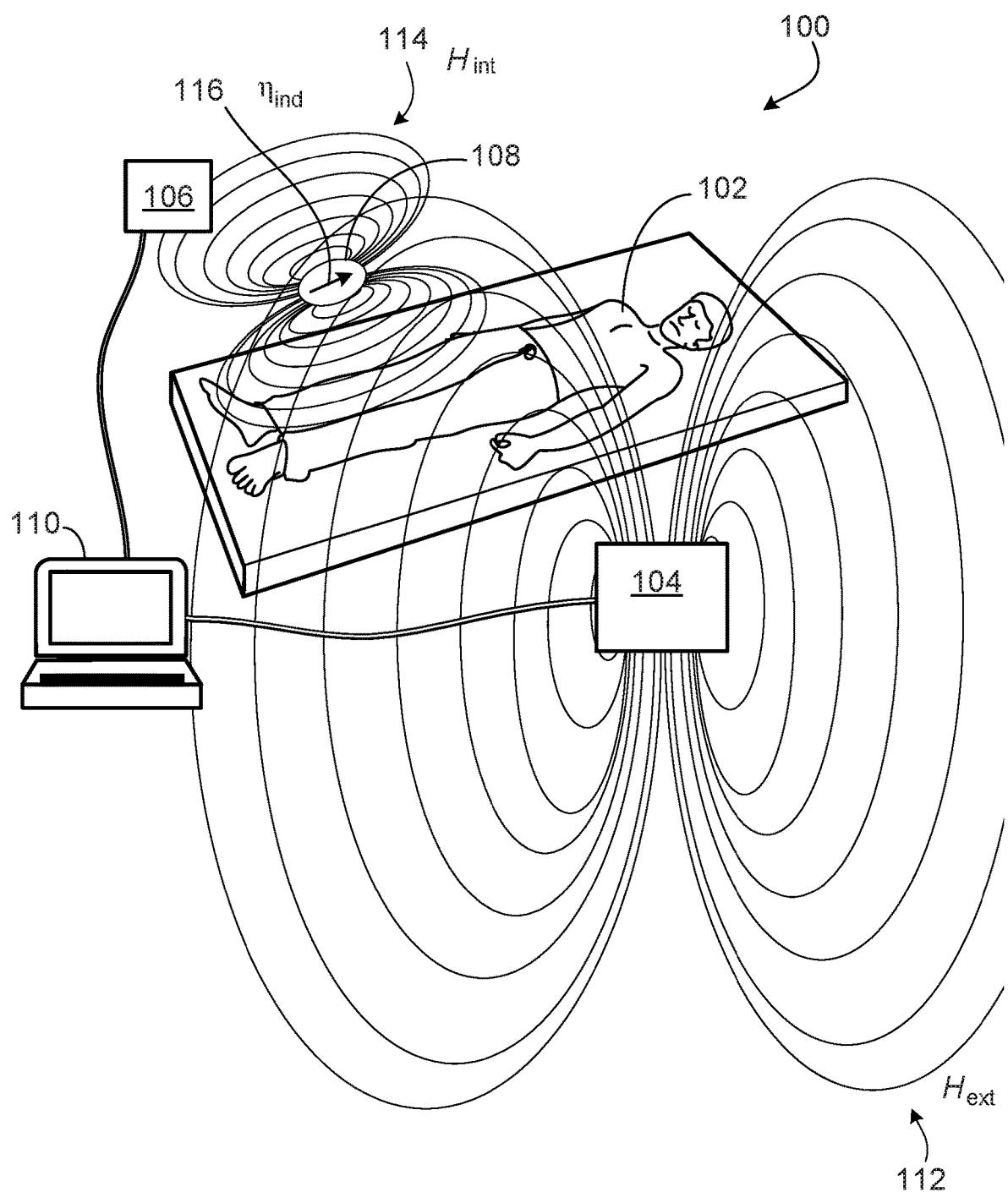
FIG. 1 is a schematic diagram of an Electromagnetic Tracking (EMT) system that includes a field generating coil, a field measuring coil, and a sensor.
Figure 2:
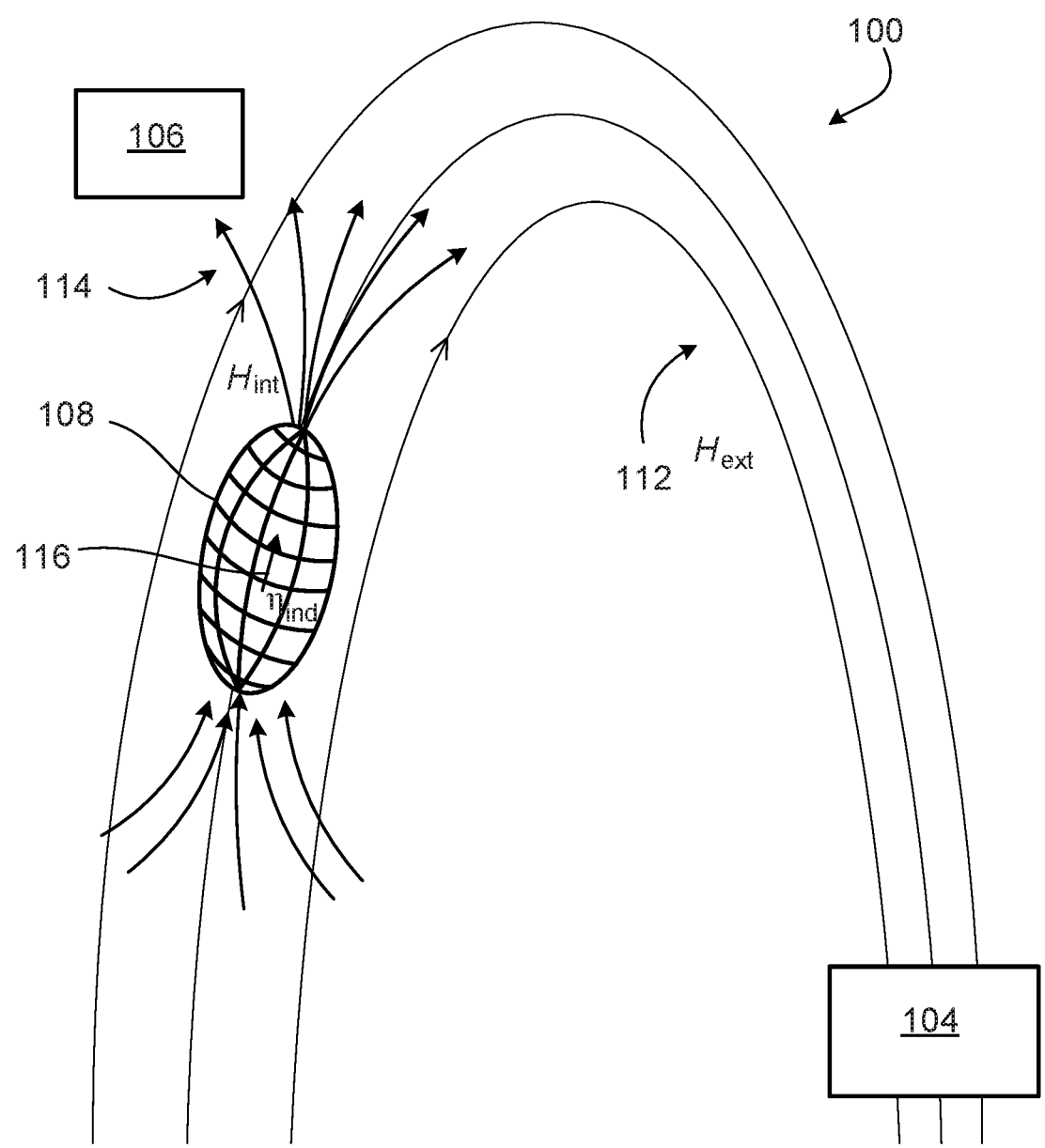
FIG. 2 shows examples of the magnetic fields present in the EMT system.

FIGS. 1 and 2 present an exemplary embodiment of an EMT system 100, which can be used for image-guided medical procedures performed on a patient 102. The system can permit targeting of an anatomical organ, structure, or vessel for visualization, diagnostic, interventional purposes, etc. In general, the system 100 includes one or more field generating coils 104 that are configured to generate a magnetic field 112 ($H_{ext}$). The system 100 also includes one or more field measuring coils 106 that are configured to measure characteristics of the magnetic field 112. When an object having magnetic properties is introduced to the system 100 (e.g., in proximity to the field generating coils 104 and/or the field measuring coils 106), the generated magnetic field 112 is distorted. The field measuring coils 106 are configured to measure characteristics of such distortions and provide the measurements to a computing device 110. The computing device 110 is configured to determine information related to the object (e.g., one or both of position and orientation information) based on the measurements.

For example, the object that is introduced to the system 100 may be a sensor 108, such as a wireless sensor 108. The sensor 108 includes a ferrofluid (304 of FIG. 3) that can have one or more magnetic properties. In particular, the ferrofluid 304 is a fluid that becomes magnetized in the presence of a magnetic field (e.g., the magnetic field 112). Thus, when the sensor 108 is in proximity to the magnetic field 112, the sensor 108 causes distortion of the magnetic field 112. In other words, the sensor 108 interacts with the magnetic field 112 generated by the field generating coils 104 to create a distorted magnetic field 114 ($H_{int}$). An induced moment 116 ($\eta_{ind}$) is also created in the sensor 108. The characteristics of the distorted magnetic field 114 can correspond to the position (e.g., x, y, z coordinates) and orientation (azimuth ($\psi$), altitude ($\theta$), roll ($\varphi$) angles) of the sensor 108. Therefore, the field measuring coils 106 can measure the characteristics of the magnetic field (e.g., the magnetic field 112 when the sensor 108 is not present and/or the distorted magnetic field 114 when the sensor 108 is present), provide a signal representative of the measured characteristics to the computing device 110, and the computing device 110 can determine one or both of the position and the orientation of the sensor 108 based on the measurements. In this way, the sensor 108 may act as a six degree of freedom (6DoF) sensor that is configured to allow for measurement of position and orientation information related to forward/back position, up/down position, left/right position, azimuth, altitude, and roll.

As illustrated in FIG. 1, the field generating coils 104 (e.g., sometimes referred to as field coils) and the field measuring coils 106 (e.g., sometimes referred to as pick-up coils) may be connected to the computing device 110 by a wired connection, although wireless connections are also possible. The location of the field generating coils 104 and the location of the field measuring coils 106 may be known to the computing device 110 (e.g., in terms of x, y, and z coordinates relative to the computing device 110). The field measuring coils 106 may measure one or more characteristics of the magnetic field 112 generated by the field generating coils 104 without the sensor being present, for example, to obtain a baseline magnetic field measurement. A signal representative of the measured characteristics may be provided to the computing device 110.

In some implementations, the field generating coils 104 may be positioned at a surgical drill, at a surgical table (e.g., incorporated into the surgical table), and/or placed somewhere at/near the patient 102. The field measuring coils 106 may be positioned at a location spaced from the field generating coils 104 (e.g., at a location different from the location of the field generating coils 104). In some implementations, the field measuring coils 106 may be positioned at the surgical drill, at the surgical table, and/or placed somewhere at/near the patient 102. In some implementations, the field generating coils 104 or the field measuring coils 106 may be incorporated into a ring that is placed around a leg of the patient 102.

In some implementations, a sensor array may be used to track the location at which the field generating coils 104 are positioned. For example, a sensor array (e.g., a repeater) may be positioned at a location spaced from the field generating coils 104 to track the location of the field generating coils 104 (and, e.g., the surgical drill). In some implementations, such as implementations in which the EMT system 100 is relatively over-determined (e.g., including a relatively large number of field generating coils 104 and field measuring coils 106, such as eight or more of each coil), a solution to the relative positions of the field generating coils 104, the field measuring coils 106, and the sensor array may be numerically determined. In such implementations, the sensor array may also be positioned at the surgical drill such that the field generating coils 104 and the sensor array have a fixed position relative to each other.

The sensor 108 may be introduced in proximity to the magnetic field 112 in a wireless manner (e.g., such that the sensor 108 is not physically connected to the computing device 110). For example, the sensor 108 may be incorporated into a medical device that is to be tracked during a medical procedure. The ferrofluid 304 of the sensor 108 (and, e.g., any other magnetic and/or metallic portions of the sensor 108) causes the magnetic field 112 generated by the field generating coils 104 to be distorted. That is, magnetic properties of the sensor 108 cause the magnetic field 112 near the sensor 108 to be distorted. Such change and/or distortion is illustrated by the distorted magnetic field 114. Characteristics of the distorted magnetic field 114 depend on the position and orientation of the sensor 108. For example, when the sensor 108 is located at a first position, the distorted magnetic field 114 may have a first shape and/or intensity; when the sensor 108 is located at a second position, the distorted magnetic field 114 may have a second shape and/or intensity; when the sensor 108 is located at the second position but has a different orientation, the distorted magnetic field 114 may have a third shape and/or intensity, etc. The field measuring coils 106 are configured to measure one or more characteristics of the distorted magnetic field 114 (e.g., characteristics that correspond to the shape and/or intensity of the magnetic field) and provide a signal representative of the measured characteristics to the computing device 110. The one or more characteristics of the distorted magnetic field 114 can include characteristics such as field strength, among others. In some implementations, the field strength projected on the field measuring coils 106 (i.e., the one field component of a 3D field vector in the local coil-coordinate system) is measured. In some implementations, full 3D knowledge may be obtained from the measurements of the characteristics of the distorted magnetic field 114.

The computing device 110 is configured to determine one or both of the position and the orientation of the sensor 108 based on the received signal representative of the measured characteristics of the distorted magnetic field 114. In some examples, the computing device 110 may determine the position and/or orientation of the sensor 108 relative to the position and/or orientation of the computing device 110, the position and/or orientation of the field generating coils 104, the position and/or orientation of the field measuring coils 106, etc. In some implementations, the computing device 110 may determine the position and/or orientation of the sensor 108 by comparing measured characteristics of the magnetic field 112 (e.g., when the sensor 108 is not present) to measured characteristics of the distorted magnetic field 114 (e.g., when the sensor 108 is present). One or more algorithms or mathematical formulas may be used to determine the position and/or orientation of the sensor 108. In some implementations, the algorithm may consider a first approximation in which an undisturbed field is known and assumed to be a dipole. The position and orientation of the dipole can be determined using one or more EM tracking techniques. The position of the dipole may then be refined by considering the orientation of the magnetization of the ferrofluid 304 of the sensor 108, which is given by the orientation of the external magnetic field 112. In some implementations, due to the non-spherical shape of the sensor 108, the dipole moment will change not only with strength, but also with orientation of the external magnetic field 112, which gives access to the orientation of the sensor 108.

Figure 3:
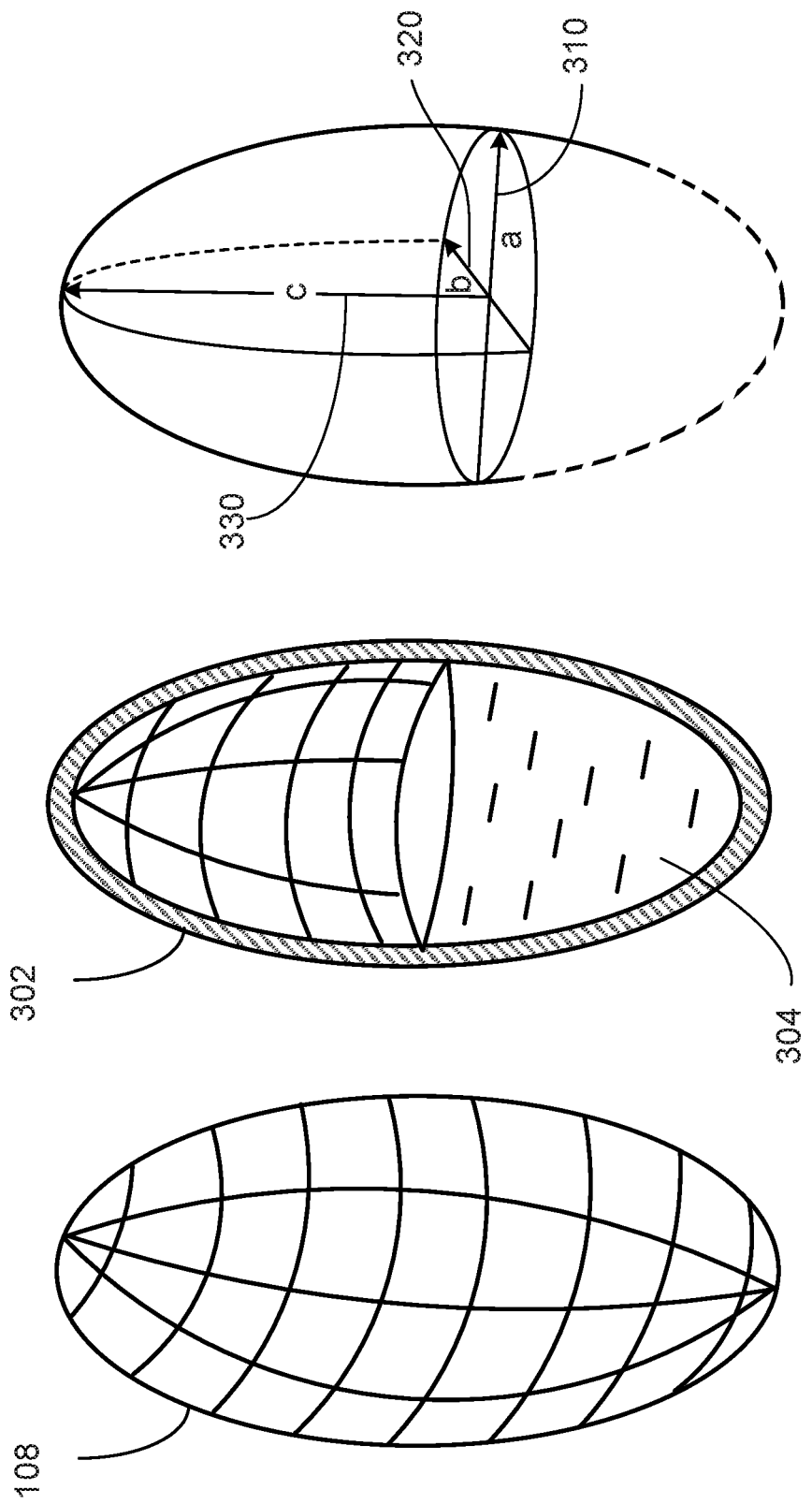
FIG. 3 shows an example of the sensor of the EMT system having an ellipsoid shape.

FIG. 3 shows an example of the sensor 108 of FIGS. 1 and 2. The sensor 108 includes a shell 302 that contains a ferrofluid 304. In the illustrated example, the sensor 108 has an ellipsoid shape that is defined by three axes: an a-axis 310, a b-axis 320, and a c-axis 330. In the illustrated example, the axes are of unequal length. That is, the a-axis 310 has a length that is not equal to a length of the b-axis 320, and the c-axis 330 has a length that is not equal to either the a-axis 310 or the b-axis 320. Such a configuration ensures that 6DoF tracking can be provided by the sensor 108. For example, because the three axes are of unequal length, the exact position and orientation of the sensor 108 can be ascertained unambiguously. If, for example, the b-axis 320 were the same length as the c-axis 330, the azimuth ($\psi$) orientation component may be unmeasurable. In some implementations, the relationship between the dimensions of the sensor 108 may be different than those shown in FIG. 3 (e.g., depending on the particular application).

The ferrofluid 304 may include any material that has magnetic properties that can influence a generated magnetic field. In some implementations, the ferrofluid 304 includes one or both of a liquid and a powder. In some implementations, the ferrofluid 304 includes iron oxide particles such as superparamagnetic iron oxide nanoparticles (SPIONs). The SPIONs may include magnetite ($Fe_3O_4$), maghemite ($\gamma$-$Fe_2O_3$), etc. In some implementations, the SPIONs may have diameters of between about 1 and 100 nanometers.

In some implementations, one or both of the shell 302 and the ferrofluid 304 may be biocompatible and/or biodegradable. For example, the shell 302 and/or the ferrofluid 304 may be made from a material that is not harmful to living tissue. In some implementations, the shell 302 is made from a polymer and/or a wax that is both biocompatible and biodegradable. In this way, the shell 302 may be left in a patient's body to decompose without harming the patient.

In some implementations, the sensor 108 may be configured to be introduced into a patient's body. For example, the sensor 108 may be incorporated into a surgical tool (e.g., a drill, a scalpel, etc.) that is to be used during a medical procedure. In some implementations, the sensor 108 may be incorporated into a surgical implant (e.g., an intramedullary (IM) nail) that is to be inserted into the patient's body. In particular, the sensor 108 may be positioned within an orifice (e.g., a screw hole) of the IM nail such that the position and/or orientation of the orifice can be tracked after the IM nail has been placed inside the patient's body (e.g., after the IM nail has been inserted into a bone of the patient). By tracking the positioned and orientation of the sensor 108, a medical professional can, for example, determine a location on the exterior of the patient's body from which a screw should be inserted in order to align with the screw hole and secure the implant in place against the bone.

In some implementations, the sensor 108 may be configured to be positioned within the patient's body at locations that are difficult to access. For example, the sensor 108 may be positioned at locations that are proximate to delicate anatomy of the patient (e.g., anatomy that, if damaged, could result in harm to the patient), such as in blood vessels (e.g., in the blood stream), in a tumor, etc.

In some implementations, the sensor 108 may be flexible (e.g., may have limited rigidity). By providing a flexible sensor 108, potential damage to the anatomy of the patient during insertion can be minimized or eliminated. In some implementations, the sensor 108 may be introduced into the patient's body in multiple stages. For example, the shell 302 may first be introduced into the patient's body, and the ferrofluid 304 may then be introduced into the patient's body. In this way, the shell 302 can be inserted into an area of the patient's body that is difficult to access (e.g., due to the reduced dimensions of the unfilled shell 302), and the ferrofluid 304 can be injected into the shell 302 thereafter. Similarly, the sensor 108 maybe removed from the patient's body in multiple stages. For example, following a medical procedure, the shell 302 may be pierced and the ferrofluid 304 may be removed. In some implementations, the ferrofluid 304 is removed by piercing the shell 302 and introducing a magnetic force (e.g., a permanent magnet) in proximity to the pierced shell 302. The shell 302 may be removed from the patient's body after removal of the ferrofluid 304. In some implementations (e.g., implementations in which the shell 302 is biocompatible and/or biodegradable), the shell 302 may be left in the patient's body.

In some implementations, the properties of the sensor 108 are such that the magnetic properties of the sensor 108 remain unchanged (or, e.g., largely unchanged) when mechanical stress is applied to the sensor 108, for example, because the ferrofluid 204 is not subject to strain and stress that would typically be seen in a solid ferromagnet (e.g., as it is a fluid). For example, the ferrofluid 204 may largely maintain its magnetic properties when the sensor 108 is exposed to mechanical stress. In this way, the sensor 108 can cause distortion of the magnetic field 112 in a defined and predictable way and allow the field measuring coils 106 to measure characteristics of the distorted magnetic field 114 that provide an accurate indication of the position and/or the orientation of the sensor 108. Such accurate measurements can be provided even when the sensor 108 is placed under stress as a result of being introduced into the patient's body.

Figure 4A:
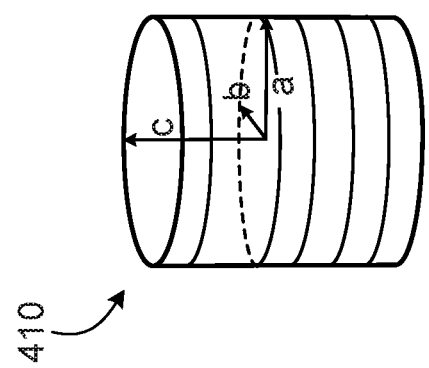
FIG. 4A-C shows other examples of a sensor for an EMT system.
Figure 4B:
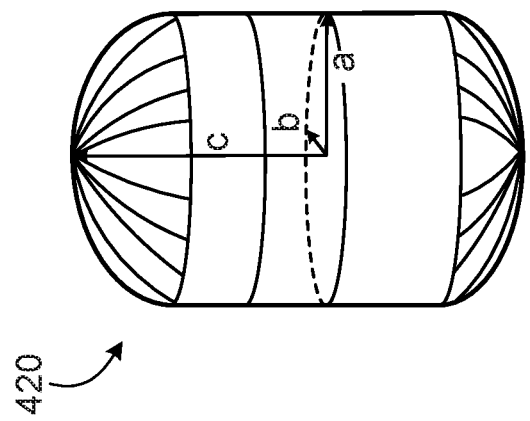
Figure 4C:
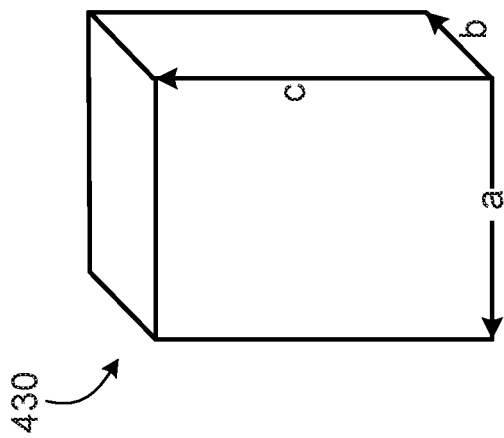

While the sensor 108 has largely been depicted as having an ellipsoid shape, other shapes are possible. FIGS. 4A-C show examples of other sensors having various shapes. As shown in FIG. 4A, in some implementations, a sensor 410 for use in the EMT system 100 may have a cylindrical shape. As shown in FIG. 4B, in some implementations, a sensor 420 for use in the EMT system 100 may have a pill shape (e.g., a cylinder with half-spheres on the top and bottom ends). As shown in FIG. 4C, in some implementations, a sensor 430 for use in the EMT system 100 may have a cuboid shape, such as a cube or a rectangular prism. The sensors 410, 420, 430 may have any of a number of dimensions. For example, as described above with respect to FIG. 3, the axes that define each of the sensors 410, 420, 430 (e.g., the a-axis, the b-axis, and the c-axis) may have lengths that are unequal. In some implementations, one or more of the axes may have lengths that are equal to lengths of one or more of the other axes.

The one or more field generating coils 104 (e.g., sometimes referred to as a transmitter) can include a single field generating coil or an array of field generating coils. Similarly, the one or more field measuring coils 106 (e.g., sometimes referred to as a receiver) can include a single field measuring coil or an array of field measuring coils. When an array of coils is used for the one or more field generating coils 106, each coil may be sequentially energized, with each coil creating its own magnetic field and eliciting a different response in the sensor 108. When an array of coils is used for the one or more field measuring coils 108, each coil may be sequentially energized during the time when each field generating coil 106 is energized, with each coil measuring characteristics of the resulting magnetic field (e.g., one or both of the magnetic field 112 and the distorted magnetic field 114).

In some implementations, one or more of the field generating coils 106 may be used for measurement purposes, and one or more of the field measuring coils 108 may be used for field generation purposes. In other words, one or more of the field generating coils 106 may act as field measuring coils 108 and/or one or more of the field measuring coils 108 may act as field generating coils 106. The field generating coils 106 and the field measuring coils 108 may have a configuration and structure that allows for such interchanging of use.

In some implementations, the EMT system 100, including the wireless sensors 108, 410, 420, 430 described herein, can be used to track a surgical implant such as an intramedullary (IM) nail during a surgical procedure. An IM nail (also known as an IM rod) is a metal rod forced into the medullary cavity of a bone to treat fractures and/or breaks of long bones of the body.

FIGS. 5A-E show a series of diagrams illustrating an IM nail being inserted into a fractured femur. A top half of the femur 502a may become separated from a bottom half of the femur 502b (FIG. 5A). A hole can be drilled in the lengthwise direction from a top surface of the top half of the femur 502a, through the top half of the femur 502a, through a top surface of the bottom half of the femur 502b, and through the bottom half of the femur 502b (FIG. 5B). An IM nail 504 can then be inserted into the femur 502 through the drilled hole (FIG. 5C). Fasteners 506 can be inserted through the patient's leg, through the femur 502, and into the IM nail 504 (FIG. 5D), thereby securing the IM nail 504 in place (FIG. 5E).

Figure 6:
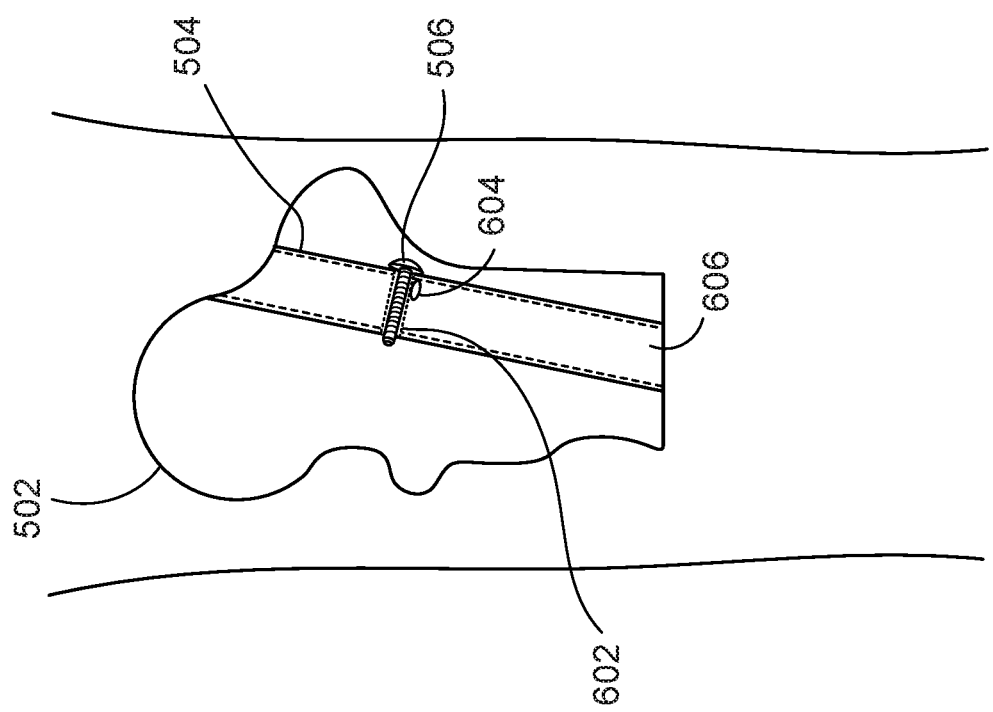
FIG. 6 shows a partial cross-sectional view of the IM nail of FIGS. 5A-E.

FIG. 6 shows a partial cross-sectional view of the IM nail 504. The IM nail includes a plurality of clearance holes 602, each configured to accept one of the fasteners 506. In some implementations, the fasteners 506 are screws that are configured to fix the IM nail 504 to the femur 502. Once the IM nail 504 is inserted into the femur 502 (e.g., by hammering the IM nail 504 into place within the drill hole), the locations of the clearance holes 602 may be difficult to determine. In some implementation, the locations of the clearance holes 602 may be determined using imaging techniques. For example, one or more X-ray images of the IM nail 504 and the clearance holes 602 can be taken, either discretely or continuously, to determine the exact location of the clearance holes 602. The fasteners 506 may then be inserted into the clearance holes 602 from the exterior of the patient's leg. However, excessive imaging may be harmful to the patient and therefore may be unfavored.

In some implementations, the IM nail 504 may be substantially hollow such that the IM nail 504 can house one or more sensors. For example, a sensor 604 (e.g., such as the sensors 108, 410, 420, 430 described above) may be positioned within a hollow cavity 606 of the IM nail 504 proximate to each of the clearance holes 602. The sensor 604 may be a six degree of freedom (6DoF) sensor that is configured to allow for measurement of position and orientation information related to forward/back position, up/down position, left/right position, azimuth, altitude, and roll. Before the IM nail 504 is inserted into the femur 502, the sensor 604 may be positioned within the cavity 606 of the IM nail 504 at a known location relative to the clearance hole 602. The sensor 604 can be tracked using the EMT system 100 described above with respect to FIG. 1. Therefore, as the position and orientation of the sensor 604 is tracked, the relative position and orientation of the clearance hole 602 can also be ascertained.

Figure 7:
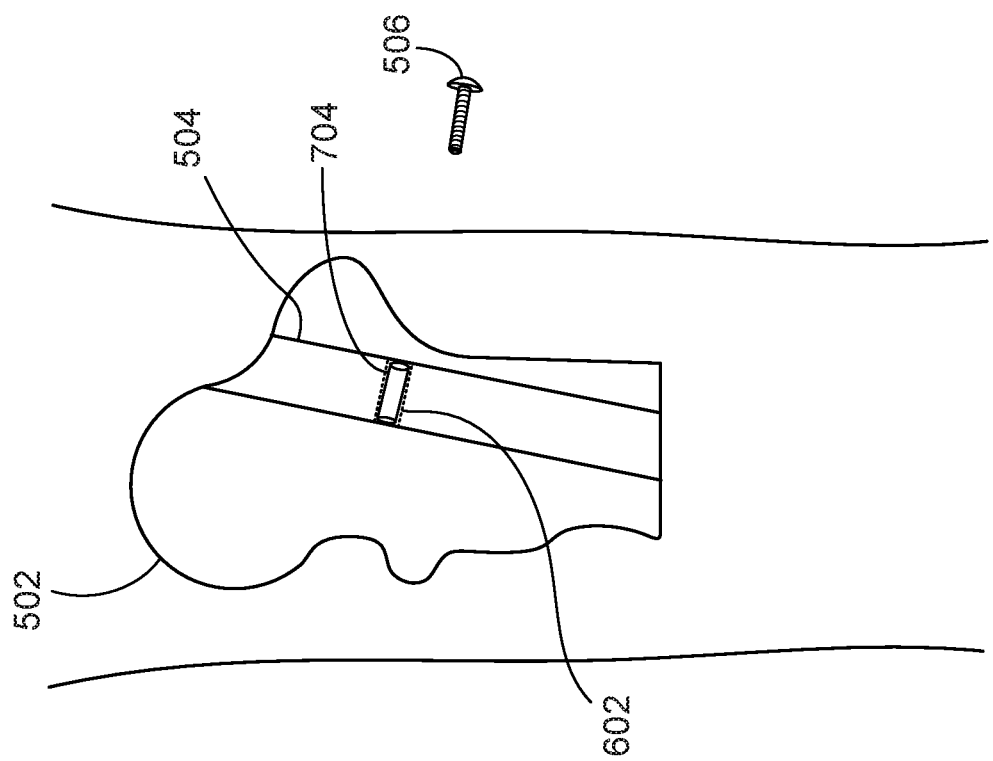
FIG. 7 shows an example of the IM nail in which a sensor is inserted into a clearance hole of the IM nail.

In some implementations, rather than the sensor 604 being positioned within the cavity 606 of the IM nail 504 proximate to the clearance hole 602, a sensor may be inserted into the clearance hole 602 itself. FIG. 7 shows an example in which a sensor 704 is positioned in the clearance hole 602 of the IM nail 504. Using the illustrated arrangement, the position and orientation of the clearance hole 602 can be directly tracked by tracking the position and orientation of the sensor 704 (e.g., rather than relying on a predetermined relationship between the location of the sensor 604 and the location of the clearance hole 602).

In the illustrated example, the sensor 704 has a cylindrical shape (e.g., like the sensor 410 of FIG. 4A). Such a cylindrical shape may be desirable for the sensor 704 because the clearance hole 602 may be known to be cylindrical. The roll component of the orientation of the sensor 704 can be discounted because the sensor 704 and the clearance hole 602 are cylindrically symmetric. In some implementations, one or more dimensions of the clearance hole 602 and one or more dimensions of the sensor 704, such as the respective diameters, are substantially similar. Therefore, in this example, the sensor 704 may be a five degree of freedom (5DoF) sensor that is configured to allow for measurement of position and orientation information related to forward/back position, up/down position, left/right position, azimuth, and altitude, (e.g., but not roll). The tracking can therefore be simplified, lower-cost hardware can be used, and the computational power to track the sensor 704 can be minimized. Further, the location of the clearance hole 602 can be determined to a higher degree of certainty and/or accuracy.

The use of a wireless sensor 704 for IM nail surgical procedures can provide a number of advantages. For example, sensors used in IM nail surgical procedures are typically wired sensors that require wires to run through the cavity of the IM nail to a computing system. Such wires may make it difficult to remove the sensor following the procedure. In some implementations, as described above, the sensor 704 described herein may be biocompatible and/or biodegradable. For example, a shell of the sensor 704 and/or a ferrofluid core of the sensor 704 may be made from a material that is not harmful to living tissue. Therefore, following the IM nail surgical procedure and once the fastener 506 has been inserted into the clearance hole 602 from the exterior of the patient's leg, the remnants of the sensor 704 can be left in the patient to safely degrade. Alternatively, some or all of the sensor 704 may be removed from the clearance hole 602 and the patient's body by introducing a magnetic force (e.g., a permanent magnet) in proximity to the sensor 704. For example, in implementations in which the sensor 704 includes a shell and a ferrofluid core, the shell of the sensor 704 may be pierced when the fastener 506 is inserted into the clearance hole 602 where the sensor 704 resides. A permanent magnet may be applied in proximity to the clearance hole 602 to pull the ferrofluid from the patient while leaving the biocompatible and/or biodegradable shell behind.

In some implementations, positioning the wireless sensor 704 within the clearance hole 602 can provide a number of advantages. During implanting, the IM nail 504 may experience external forces. Such external forces may naturally occur due to stress applied to the IM nail 504 (e.g., when the IM nail 504 is hammered into a bone). Such external forces may cause the IM nail 504 to bend. The bend may cause the position and orientation of the clearance hole 602 relative to a sensor that is not positioned within the clearance hole 602 to change, thereby resulting in positioning errors. On the other hand, if the wireless sensor 704 is positioned within the clearance hole 602, changes to the position and orientation of the clearance hole 602 due to deformation of the IM nail 504 are correspondingly experienced by the wireless sensor 704.

In some implementations, mirror symmetry in the EMT system 100 may be minimized and/or eliminated by employing a technique that utilizes empirical knowledge (e.g., a history of know positions and/or orientations of the sensor).

The EMT system 100 described above can be implemented using software included on a computer-readable medium for execution on a computer (e.g., the computing device 110 of FIG. 1). For example, the software may form procedures in one or more computer programs that execute on one or more programmed or programmable computer systems (which may be of various architectures).

FIG. 8 is a block diagram of an example computer system 800. The computing device 110 of FIG. 1 may be an example of the computer system 800 described here. The system 800 can include a processor 810, a memory 820, a storage device 830, and an input/output device 840. Each of the components 810, 820, 830, and 840 can be interconnected, for example, using a system bus 850. The processor 810 is capable of processing instructions for execution within the system 800. The processor 810 can be a single-threaded processor, a multi-threaded processor, or a quantum computer. The processor 810 is capable of processing instructions stored in the memory 820 or on the storage device 830. The processor 810 may execute operations such as causing the EMT system 100 to determine the position and/or the orientation of the sensor 108.

The memory 820 stores information within the system 800. In some implementations, the memory 820 is a computer-readable medium. The memory 820 can, for example, be a volatile memory unit or a non-volatile memory unit.

The storage device 830 is capable of providing mass storage for the system 800. In some implementations, the storage device 830 is a non-transitory computer-readable medium. The storage device 830 can include, for example, a hard disk device, an optical disk device, a solid-date drive, a flash drive, magnetic tape, or some other large capacity storage device. The storage device 830 may alternatively be a cloud storage device, e.g., a logical storage device including multiple physical storage devices distributed on a network and accessed using a network. In some implementations, the information stored on the memory 820 can also or instead be stored on the storage device 830.

The input/output device 840 provides input/output operations for the system 800. In some implementations, the input/output device 840 includes one or more of network interface devices (e.g., an Ethernet card), a serial communication device (e.g., an RS-232 10 port), and/or a wireless interface device (e.g., a short-range wireless communication device, an 802.11 card, a 3G wireless modem, or a 4G wireless modem). In some implementations, the input/output device 840 includes driver devices configured to receive input data and send output data to other input/output devices, e.g., a keyboard, a printer, and display devices. In some implementations, mobile computing devices, mobile communication devices, and other devices are used.

In some implementations, the system 800 is a microcontroller. A microcontroller is a device that contains multiple elements of a computer system in a single electronics package. For example, the single electronics package could contain the processor 810, the memory 820, the storage device 830, and input/output devices 840.

Although an example computer system has been described in FIG. 8, implementations of the subject matter and the functional operations described above can be implemented in other types of digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible program carrier, for example a computer-readable medium, for execution by, or to control the operation of, a processing system. The computer readable medium can be a machine readable storage device, a machine readable storage substrate, a memory device, a composition of matter effecting a machine readable propagated signal, or a combination of one or more of them.

The term "computer system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM and DVD-ROM disks. The processor and the memory can be supplemented by, or incorporated in, special purpose logic circuitry. The components of the system can be interconnected by any form or medium of digital data communication, e.g., a communication network. Examples of communication networks include a local area network ("LAN") and a wide area network ("WAN"), e.g., the Internet.

A number of embodiments have been described. Nevertheless, it will be understood that various modifications may be made without departing from the spirit and scope of the subject matter described herein. Other such embodiments are within the scope of the following claims.

What is claimed is:

1. A system comprising:
   a sensor configured to be introduced into a clearance hole of a surgical implant, the sensor having a three-dimensional orthogonal geometry, wherein each orthogonal dimension of the sensor has a different length, wherein the sensor is configured to be introduced in proximity to a generated magnetic field and cause distortion of the magnetic field; and
   one or more field measuring coils configured to:
      measure a characteristic of the magnetic field when the sensor is in proximity to the magnetic field; and
      provide, to a computing device, a signal representative of the measured characteristic of the magnetic field,
   wherein the computing device is configured to determine a position and an orientation of the sensor and the clearance hole based on the measured characteristic of the magnetic field.

2. The system of claim 1, wherein the surgical implant is an intramedullary (IM) nail.

3. The system of claim 2, wherein the IM nail is configured to be inserted into a femur of a patient.

4. The system of claim 3, wherein a fastener is configured to be inserted into the clearance hole from a location at the exterior of a leg of the patient, wherein the location at the exterior of the leg of the patient is identified based on the determined one or both of the position and an orientation of the sensor and the clearance hole.

5. The system of claim 1, wherein the sensor has a cylindrical shape.

6. The system of claim 5, wherein the sensor and the clearance hole are cylindrically symmetrical.

7. The system of claim 5, wherein a diameter of the sensor is substantially equal to a diameter of the clearance hole.

8. The system of claim 1, wherein the sensor is a five degree of freedom (5DoF) sensor.

9. The system of claim 1, wherein the sensor comprises a shell that contains a ferrofluid.

10. The system of claim 9, wherein one or both of the shell and the ferrofluid are one or both of biocompatible and biodegradable.

11. The system of claim 9, wherein the ferrofluid comprises one or both of a liquid and a powder.

12. The system of claim 9, wherein the ferrofluid comprises superparamagnetic iron oxide nanoparticles (SPIONs).

13. The system of claim 12, wherein the SPIONs comprise one or both of magnetite ($Fe_3O_4$) and maghemite ($\gamma$-$Fe_2O_3$).

14. The system of claim 9, wherein the shell comprises a polymer.

15. The system of claim 9, wherein the ferrofluid is configured to be removed from the shell by piercing the shell and introducing a magnetic force in proximity to the shell.

16. The system of claim 15, wherein the shell is pierced by a fastener that is inserted into the clearance hole.

17. The system of claim 1, wherein the sensor is wireless.

18. The system of claim 1, wherein the sensor has an ellipsoid shape.

19. A method comprising:
- introducing a sensor into a clearance hole of a surgical implant, wherein the sensor is configured to be introduced in proximity to a generated magnetic field and cause distortion of the magnetic field, the sensor having a three-dimensional orthogonal geometry, wherein each orthogonal dimension of the sensor has a different length;
- receiving, by a computing device, from one or more field measuring coils, a signal representative of a characteristic of the magnetic field measured when the sensor is in proximity to the magnetic field; and
- determining, by the computing device, a position and an orientation of the sensor and the clearance hole based on the measured characteristic of the magnetic field.

20. The method of claim 19, further comprising receiving, by the computing device, from the one or more field measuring coils, a signal representative of a characteristic of the magnetic field measured when the sensor is not in proximity to the magnetic field.

21. The method of claim 20, wherein determining the position and the orientation of the sensor and the clearance hole comprises comparing the characteristic of the magnetic field measured when the sensor is not in proximity to the magnetic field and the characteristic of the magnetic field measured when the sensor is in proximity to the magnetic field.

\* \* \* \* \*